United States Patent [19]

Meyer et al.

[11] Patent Number: 4,478,598
[45] Date of Patent: Oct. 23, 1984

[54] AMPHOTERIC STYRENE DERIVATIVES USEFUL AS FLUORESCENT BRIGHTENERS

[75] Inventors: Hans R. Meyer, Binningen; Max Morf, Schönenbuch, both of Switzerland

[73] Assignee: Ciba-Geigy Corporation, Ardsley, N.Y.

[21] Appl. No.: 350,837

[22] Filed: Feb. 22, 1982

[30] Foreign Application Priority Data

Feb. 26, 1981 [CH] Switzerland ............... 1295/81

[51] Int. Cl.³ .................. C11D 3/42; D06L 3/12
[52] U.S. Cl. .................... 8/648; 252/8.75; 252/8.8; 252/301.21; 252/301.35; 252/524; 252/526; 252/527; 252/543; 252/545; 252/546; 260/459 A; 260/465 D; 427/158; 546/255; 260/239 B; 544/111; 544/158; 544/159; 544/169; 544/172; 544/174; 544/357; 544/359; 546/192; 546/208; 548/518; 548/531
[58] Field of Search ............ 252/301.21, 301.35, 252/301.26, 524, 526, 527, 543, 545, 546, 8.75, 8.8; 260/459 A, 465 D; 542/459; 546/255; 564/286; 8/648; 427/158

[56] References Cited

U.S. PATENT DOCUMENTS 3,339,393 7/1982 Luthi ..................... 260/459 A
3,394,174 7/1968 Feigin ..................... 260/509
3,547,986 12/1970 Falcone ................... 260/501.13
3,660,470 5/1972 Hirst ..................... 260/501.12
3,663,538 5/1972 Heinz ..................... 252/543
3,757,010 9/1973 Balzer .................... 252/543
3,822,305 7/1974 Ulrich .................... 260/465 D
4,009,193 2/1977 Scheuermann ............... 252/301.22
4,263,431 4/1981 Weber .................... 252/301.22
4,294,711 10/1981 Hardy .................... 252/8.75

4,314,820 2/1982 Weber ..................... 8/648

Primary Examiner—Dennis L. Albrecht
Attorney, Agent, or Firm—Edward McC. Roberts

[57] ABSTRACT

The amphoteric styrene derivatives correspond to the formula

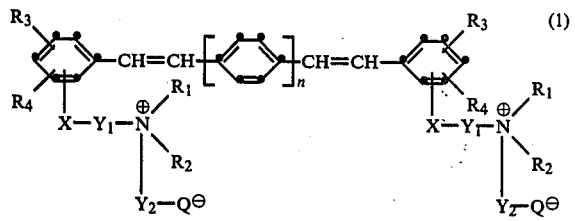

in which X is oxygen, sulfur, a direct bond, $-SO_2N(-R_5-)$, $-CON(R_5-)$ or $-COO-$, $Y_1$ and $Y_2$ independently of one another are $C_1-C_4$-alkylene or hydroxypropylene, $R_1$ and $R_2$ independently of one another are $C_1-C_4$-alkyl or, together with the N atom, are a pyrrolidine, piperidine, hexamethyleneimine or morpholine ring, and $R_1$, together with $R_5$, is also a piperazine ring, $R_3$ and $R_4$ are hydrogen, $C_{1-4}$-alkyl, chlorine, $C_{1-4}$-alkoxy or $C_{3-4}$-alkenyl or together, in the o-position relative to one another, are a trimethylene or tetramethylene group, $R_5$ is hydrogen, $C_{1-4}$-alkyl or cyanoethyl or, together with $R_1$, is a piperazine ring, Q is $-COO$ or $-SO_3$ and n is the number 1 or 2, and can be prepared by reacting the corresponding amine compounds with a halide of the formula $Hal-Y_2-QH$ and saponifying the quaternary ammonium halides eventually formed. They can be used for the fluorescent brightening of organic materials.

14 Claims, No Drawings

AMPHOTERIC STYRENE DERIVATIVES USEFUL AS FLUORESCENT BRIGHTENERS

The present invention relates to novel amphoteric styrene derivatives, processes for their preparation, their use for the fluorescent brightening of organic materials, and also detergents and laundry treatment agents containing these amphoteric styrene derivatives.

Cationic distyrylbenzene compounds and distyrylbiphenyl compounds which give a strong white effect on cotton, in clean washing liquors, in the presence of cationic softeners, are known from European Patent Application Nos. 19,078 and 19,702. However, these effects are reduced by the presence of relatively large amounts of human skin grease which is dissolved out during washing.

The object of the present invention was to find brighteners which do not possess this disadvantage.

It has now been found that amphoteric styrene derivatives are insensitive towards the soil corresponding to human skin grease.

The amphoteric styrene derivatives according to the invention correspond to the formula

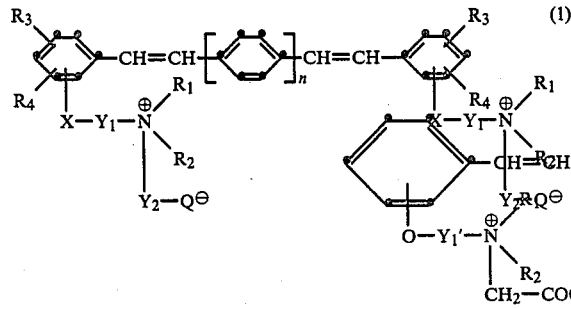

in which X is oxygen, sulfur, a direct bond, —SO$_2$N(R$_5$)—, —CON(R$_5$)— or —COO—, Y$_1$ and Y$_2$ independently of one another are C$_1$-C$_4$-alkylene or hydroxypropylene, R$_1$ and R$_2$ independently of one another are C$_1$-C$_4$-alkyl or, together with the N atom, are a pyrrolidine, piperidine, hexamethyleneimine or morpholine ring, and R$_1$, together with R$_5$, is also a piperazine ring, R$_3$ and R$_4$ are hydrogen, C$_{1-4}$-alkyl, chlorine, C$_{1-4}$-alkoxy or C$_{3-4}$-alkenyl or together, in the o-position relative to one another, are a trimethylene or tetramethylene group, R$_5$ is hydrogen, C$_{1-4}$-alkyl or cyanoethyl or, together with R$_1$, is a piperazine ring, Q is —COO or —SO$_3$ and n is the number 1 or 2.

In the context of the amphoteric styrene derivatives of the formula (1), according to the invention, there are, in particular, those which correspond to the formula

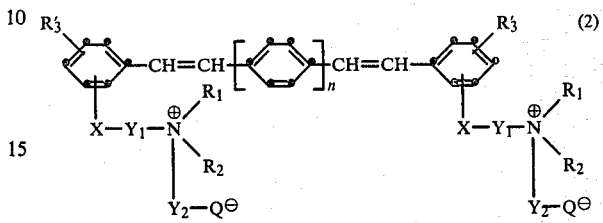

in which R$_1$, R$_2$, Y$_1$, Y$_2$, Q and n are as defined above, X$_1$ is oxygen, a direct bond, —CONH— or —COO— and R'$_3$ is hydrogen, C$_{1-4}$-alkyl, methoxy or chlorine.

Preferred amphoteric styrene derivatives are those of the formula

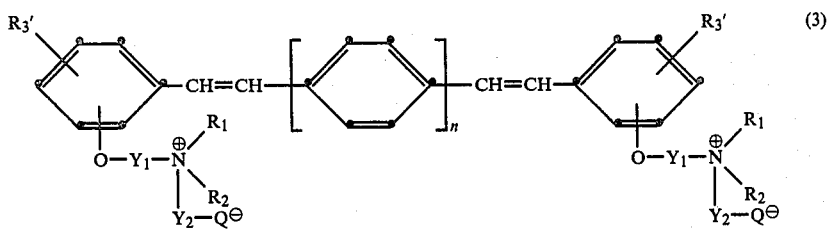

in which R$_1$, R$_2$, R'$_3$, Y$_1$, Y$_2$, Q and n are as defined above.

The amphoteric styrene derivatives of the formula

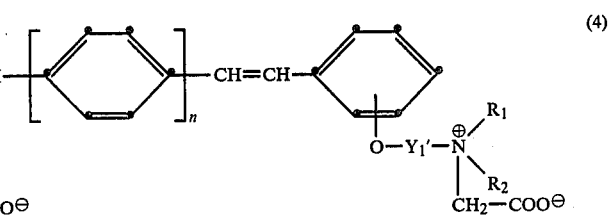

in which Y'$_1$ is C$_{1-4}$-alkylene and R$_1$, R$_2$ and n are as defined above, are particularly preferred.

In the preceding formulae (1) to (4), X is preferably oxygen, a direct bond or the —CONH— group, R$_1$ and R$_2$ are preferably C$_{1-4}$-alkyl, R$_3$ is preferably hydrogen, chlorine, C$_{1-4}$-alkyl or C$_{1-4}$-alkoxy, R$_4$ and R$_5$ are preferably hydrogen, X$_1$ is preferably oxygen or a direct bond, Y$_1$ and Y$_2$ are preferably C$_{1-4}$-alkylene, R'$_3$ is preferably hydrogen, methyl, methoxy or chlorine, Q is preferably the —COO— group and Y$_2$ is preferably the —CH$_2$— group.

A further object of the present invention is a process for the preparation of the novel amphoteric styrene derivatives, which comprises reacting a styrene derivative of the formula

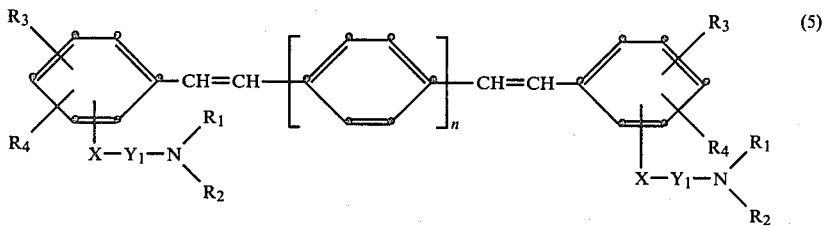

in which $R_1$, $R_2$, $R_3$, $R_4$, $X$, $Y_1$ and $n$ are as defined above, with a halide of the formula

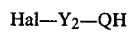

in which $Y_2$ and $Q$ are as defined above and Hal is chlorine or bromine, or, if $Q=-COO$, with its salts, esters, amides, nitriles or lactones, or, if $Q=-SO_3$, with its salts, aryl esters or sultones, or, if $Y_2=$hydroxypropylene, also with the corresponding epoxides, and saponifying the quaternary ammonium halides formed in all cases. Lactones, sultones and epoxides are to be understood as meaning the dehydrohalogenation products of the compounds of the formula Hal—$Y_2$—QH.

Betaines or betaine-like compounds exist in amphoteric form over a wide pH range. Under relatively strongly acidic conditions, they become cationic. Carboxylic acids can then be present in the form of their acid adducts, i.e. in the form of their salts, containing a free carboxyl group, of the type

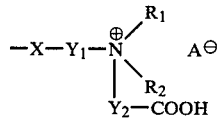

in which $A^\ominus$ is the anion of the acid. However, the required acidity is generally outside the practical range for washing fabrics. They are easily obtained by adding an inorganic or organic acid HA to the amphoteric compound.

Examples of acids HA which can be used are hydrohalic acids such as hydrochloric acid and hydrobromic acid, dialkyl phosphates, methanephosphonic acid, formic acid, acetic acid, propionic acid, glycolic acid, lactic acid, malic acid, tartaric acid, mucic acid, gluconic acid, citric acid, levulinic acid and acrylic acid.

Preferred alkylating agents are halogenocarboxylic acids and their alkali metal salts and lower alkyl esters, for example chloroacetic acid, bromoacetic acid, sodium chloroacetate, ethyl 2-chloroacetate, ethyl 2-bromoacetate, methyl 2-bromopropionate and ethyl 4-bromobutyrate; halogenoalkanesulfonates, for example sodium 2-bromoethanesulfonate, phenyl 2-bromoethanesulfonate, sodium 3-chloro-2-hydroxy-propane-1-sulfonate and sodium bromomethanesulfonate; alkanesultones such as 1,3-propanesultone and 1,4-butanesultone, and also epoxyalkanesulfonates such as sodium 2,3-epoxypropane-1-sulfonate. The latter is advantageously used in the presence of an acid or of a salt of the amine used.

Amphoteric sulfonic acids of the formula (1) in which $Q$ is $SO_3$ and $Y_2$ is hydroxypropyl are also obtained by quaternising compounds of the formula (5) with glycerol dihalogenohydrins or with a hydrogen halide and epihalogenohydrins to give compounds of the formula

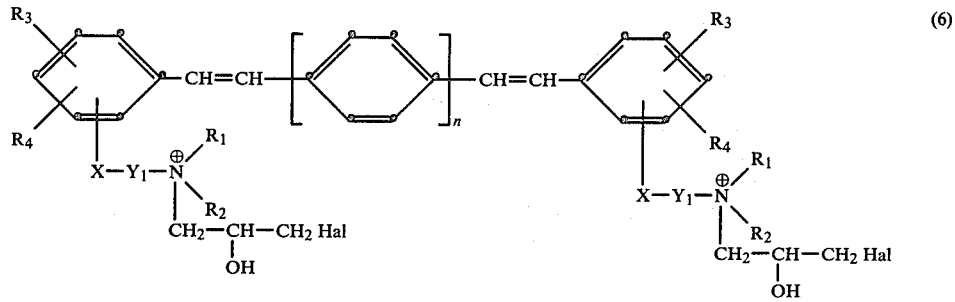

in which $R_1$, $R_2$, $R_3$, $R_4$, $X$, $Y_1$ and $n$ are as defined above and Hal is Cl or Br, and then reacting these compounds with alkali metal or alkaline earth metal bisulfites according to P. Nikolaus, Fette, Seifen, Anstrichmittel 74, 328–331 (1972).

Compounds of the formula (1) in which $Q$ is $SO_3$ and $Y_2$ is propylene are also obtained by quaternising compounds of the formula (5) with allyl chloride or allyl bromide, and then reacting the resulting compounds of the formula

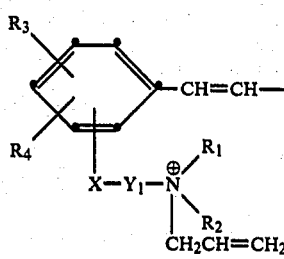 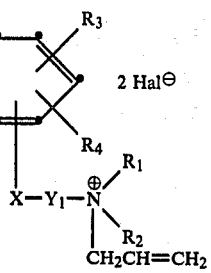

(7)

in which $R_1$, $R_2$, $R_3$, $R_4$, $X$, $Y_1$ and $n$ are as defined above and Hal is Cl or Br, with alkali metal or alkaline earth metal bisulfites according to J. of American Oil Chem. Soc. 53, 60–63 (1976); 54, 294–296 (1977).

If halogenocarboxylic acids are used as alkylating agents, then it is advantageous to add at least the stoichiometric amount of a base. Suitable bases are alkali metal or alkaline earth metal hydroxides or alcoholates, such as sodium hydroxide or sodium methylate, in particular alkali metal and alkaline earth metal salts of weak acids, such as sodium carbonate, potassium carbonate or calcium carbonate, or alkaline earth metal oxides such as magnesium oxide in finely divided form. Tertiary amines which are difficult to quaternise, such as triisopropanolamine or 2,6-di-tert.-butylpyridine, can also be used as acid acceptors. In a particularly favourable process, the alkali metal or alkaline earth metal salts of the halogenocarboxylic acids, for example the sodium salt of chloroacetic acid, are used directly.

If the esters, amides or nitriles are used as derivatives of the halogenocarboxylic acids, the corresponding quaternary ammonium halides are primarily formed and these are saponified to give the compounds of the formula (1) under acid or, preferably, alkaline conditions. Particularly suitable halogenocarboxylic acid derivatives are the esters such as alkyl chloroacetates or bromoacetates having 1 to 4 C atoms in the alkyl moiety, for example methyl or ethyl chloroacetate. Examples of amides and nitriles are chloroacetamide and chloroacetonitrile. Anhydrides and lactones, in particular β-lactones of the corresponding hydroxycarboxylic acids, such as chloroacetic anhydride or β-propiolactone, can also be used. Tosylates of the corresponding hydroxycarboxylic acids can also be used as alkylating agents in place of the halogenocarboxylic acids.

The reaction temperature can be kept within wide limits between about 20° C. and 150° C., preferably 40°–140° C., depending on the reactivity of the quaternising agent used. In general, all inert solvents are suitable as reaction media in which the quaternisation can be carried out. Preferred solvents are those which dissolve the starting material and from which the end product immediately separates out. Examples are: aromatic hydrocarbons such as benzene, toluene and xylene; halogenohydrocarbons such as dichloroethane, trichloroethane, tetrachloroethylene, chlorobenzene or dichlorobenzene; also nitro compounds such as nitromethane, nitropropane and nitrobenzene; alkanols and open-chain or cyclic ethers, such as methanol, ethanol, isopropanol, butanol, dibutyl ether, ethylene glycol, ethylene glycol monomethyl ether, ethylene glycol monoethyl ether, anisole or dioxane; ketones such as cyclohexanone or methyl ethyl ketone; fatty acid amides such as dimethylformamide or dimethylacetamide; sulfoxides such as dimethyl sulfoxide, and carboxylic acid esters or nitriles, such as ethyl acetate, butyl acetate, acetonitrile or methoxypropionitrile. In the case of quaternising agents which are sparingly soluble in organic solvents, the reaction is advantageously carried out in water or in mixtures containing water.

The saponification of the resulting quaternary ammonium halides is carried out using aqueous acids, for example catalytic amounts of mineral acids such as hydrochloric acid or sulfuric acid, or, preferably, bases such as alkali metal or alkaline earth metal hydroxides, in at least stoichiometric amounts, in water and/or in water-miscible organic solvents, for example alcohols, at temperatures from about 40°–110° C.

If desired, the quaternisation and saponification can also be carried out in a one-pot process.

Another method for the preparation of the amphoteric styrene derivatives of the formula (1) consists in reacting compounds of the formula

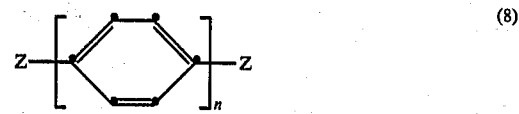

(8)

with aldehydes of the formula

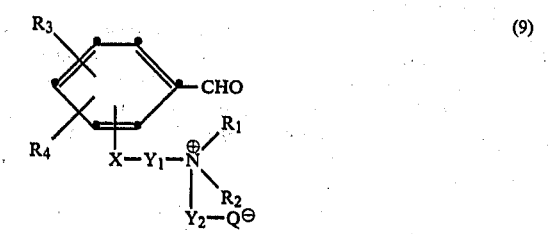

(9)

in a molecular ratio of 1:2, in a manner known per se, in the presence of a strong base, in which formulae $X$, $Y_1$, $Y_2$, $R_1$, $R_2$, $R_3$, $R_4$, $Q$ and $n$ are as defined above and $Z$ is a group of the formula

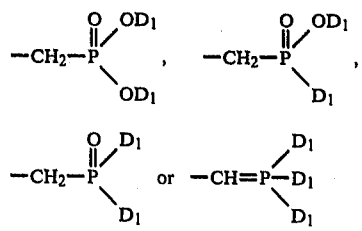

in which $D_1$ is an unsubstituted or substituted alkyl, aryl, cycloalkyl or aralkyl radical.

The amount of the base to be used is at least 1 equivalent per mol of aldehyde. In place of the compounds of the formula (9), it is also possible to use their acid adducts of the formula

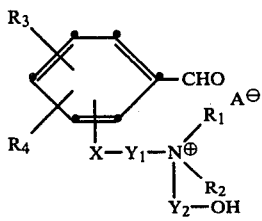
(10)

in which X, Y₁, Y₂, R₁, R₂, R₃, R₄ and A are as defined above and Q is preferably —COO—. In this case, at least 2 equivalents of base are required per mol of aldehyde.

The condensation is advantageously carried out in inert solvents. Examples of these are hydrocarbons such as toluene and xylene, or alcohols such as methanol, ethanol, isopropanol and butanol, glycols, glycol ethers such as 2-methoxyethanol, hexanols, cyclohexanol and cyclooctanol, and also ethers such as diisopropyl ether, tetrahydrofuran and dioxane, and dimethyl sulfoxide, formamide and N-methylpyrrolidone. Polar organic solvents such as dimethylformamide and dimethyl sulfoxide are particularly suitable. Some of the reactions can also be carried out in aqueous solution.

The temperature at which the reaction is carried out can vary within wide limits. It is determined by:
(α) the stability of the solvent used towards the reactants, in particular towards the strongly basic alkali metal compounds,
(β) the reactivity of the reactants in the condensation and
(γ) the activity of the solvent/base combination as a condensation agent.

Accordingly, in practice, temperatures between about 10° and 100° C. are generally suitable. If dimethylformamide is used as the solvent, the preferred temperature range is 20° to 60° C.

Possible strongly basic alkali metal compounds are, in particular, the hydroxides, amides and alcoholates (preferably of alcohols containing 1 to 4 carbon atoms) of the alkali metals, those of lithium, sodium and potassium being of predominant interest for economic reasons. However, in principle and in particular cases, alkali metal sulfides and carbonates, aryl-alkali metal compounds, for example phenyl-lithium, or strongly basic amines (including ammonium bases), for example trialkylammonium hydroxides, can also be used successfully.

The starting materials of the formulae (9) and (10) are obtained by quaternising the compounds of the formula

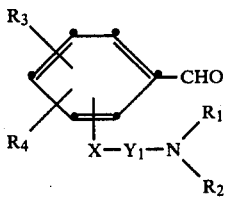
(11)

in which X, Y₁, R₁, R₂, R₃ and R₄ are as defined above, with a halide of the formula Hal—Y₂—QH or with salts, esters or lactones thereof, analogously to the quaternisation of the styrene derivatives of the formula (5), and saponifying the quaternary ammonium halides formed in all cases. The saponification is carried out in this case with the stoichiometric amount of a base or, preferably, with an acid H-Hal of the halide used. The amphoteric compounds of the formula (9) are also obtained by neutralising the products of the formula (10) formed by acid saponification.

By the procedures described, it is possible to obtain concentrated, stable aqueous solutions of the novel amphoteric styrene derivatives, which, apart from water, also contain additional solvents, for example an alcohol from the preceding ester hydrolysis, and the saponification product of the excess quaternising agent, for example glycolic acid, and also alkali metal halide.

Thus, the invention also relates to concentrated aqueous solutions, which are stable on storage, of amphoteric styrene derivatives of the formula (1), which contain (a) 0.1 to 50 percent by weight of an amphoteric styrene derivative of the formula

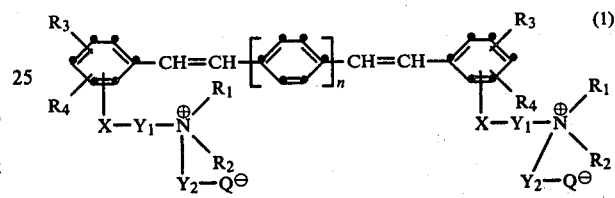
(1)

in which X is oxygen, sulfur, a direct bond, —SO₂N(-R₅—, —CON(R₅— or —COO—, Y₁ and Y₂ independently of one another are C₁-C₄-alkylene or hydroxypropylene, R₁ and R₂ independently of one another are C₁-C₄-alkyl or, together with the N atom, are a pyrrolidine, piperidine, hexamethyleneimine or morpholine ring, and R₁, together with R₅, is also a piperazine ring, R₃ and R₄ are hydrogen, C₁₋₄-alkyl, chlorine, C₁₋₄-alkoxy or C₃₋₄-alkenyl or together, in the o-position relative to one another, are a trimethylene or tetramethylene group, R₅ is hydrogen, C₁₋₄-alkyl or cyanoethyl or, together with R₁, is a piperazine ring, Q is —COO or —SO₃ and n is the number 1 or 2, (b) 0 to 20 percent by weight of the alkali metal halide formed from the quaternising agent and saponifying agent used, and (c) water.

The solutions according to the invention are also suitable for the brightening of polyacrylonitrile fibres in the gel state. They are chemically and physically stable over prolonged periods of time, when stored under the varying temperatures which prevail, i.e. neither decomposition nor separating-out of the solid product takes place, not even after dilution with any amount of water. Furthermore, salts dried on the surface by evaporation remain water-soluble.

In the dissolved or finely divided state, the novel compounds defined above show a more or less pronounced fluorescence. They can be used for the fluorescent brightening of a wide variety of synthetic, semi-synthetic or natural organic materials, or substances which contain such organic materials.

The organic materials which are to undergo fluorescent brightening can be in the most diverse states of processing (raw materials, semi-finished goods or finished goods). The compounds to be used according to the invention are important, inter alia, for the treatment of textile organic materials, in particular textile fabrics. Depending on the type of brightener compound used, it can prove advantageous to carry out the process in a neutral or alkaline or acid bath.

The novel fluorescent brighteners according to the present invention can also be used for the fluorescent brightening of paper pulps, inter alia in the presence of, for example, cationic retention agents and other additives.

The novel fluorescent brighteners according to the present invention can be employed in the following use forms:

(a) in mixtures with dyes (shading) or pigments (coloured pigments or especially, for example, white pigments), or as an additive to dyebaths;

(b) in mixtures with wetting agents, softeners, swelling agents or antioxidants;

(c) in combination with diverse textile finishing processes, for example flameproof finishes, soft-handle finishes, anti-soiling finishes or antistatic finishes, or antimicrobial finishes;

(d) by incorporation of the fluorescent brighteners into polymeric carriers (polymerisation, polycondensation or polyaddition products), in dissolved or dispersed form, for use, for example, in coating agents, impregnating agents or binders (solutions, dispersions and emulsions) for textiles, nonwovens, paper and leather;

(e) as additives to a wide variety of industrial products, in order to render these more marketable (for example improving the appearance of soaps, detergents and textile treatment agents, and pigments);

(f) in combination with other fluorescent brightener substances;

(g) in spinning bath preparations, i.e. as additives to spinning baths which are used for improving the slip for the further processing of synthetic fibres, or from a special bath before the stretching of the fibres, for example as an after-treatment of wet-spun polyacrylic fibres in the so-called gel state;

(h) for various purposes of a photographic nature, for example for electrophotographic reproduction or supersensitising;

(i) depending on the substitution, as laser dyes.

If the brightening process is combined with textile treatment or finishing methods, the combined treatment can in many cases advantageously be carried out with the aid of appropriate stable preparations which contain the fluorescent brightener compounds in a concentration such that the desired brightening effect is achieved.

The amount of the novel fluorescent brighteners to be used according to the invention, based on the material which is to undergo fluorescent brightening, can vary within wide limits. A marked and lasting effect can be obtained even with very small amounts in certain cases, for example with amounts of 0.0001 percent by weight. However, it is also possible to use amounts of up to about 0.8 percent by weight and, where necessary, up to about 2 percent by weight. For most practical purposes, it is preferable to use amounts of between 0.0005 and 0.5 percent by weight.

For various reasons, it is frequently advantageous not to use the fluorescent brighteners by themselves, i.e. pure, but mixed with a wide variety of assistants and extenders.

The novel fluorescent brighteners are also particularly suitable for use as additives to washing liquors or heavy-duty and domestic detergents and laundry after-treatment agents, to which they can be added in various ways. They are appropriately added to washing liquors in the form of their solutions in water or organic solvents, or also, in finely divided form, as aqueous dispersions. They are advantageously added to domestic or heavy-duty detergents at any stage of the manufacturing process of the detergents. They can be added either in the form of a solution or dispersion in water or other solvents, or, without assistants, as a dry brightener powder. For example, the brighteners can be dissolved in the detergent substances or mixed, kneaded or ground with the latter and, in this form, mixed with the finished detergent. However, they can also be sprayed in a dissolved or pre-dispersed form onto the finished detergent.

The compounds according to the invention can also be employed in an after-rinse bath such as is conventionally used for merely imparting a soft handle, antistatic properties, anti-soil effects, scents and the like. In particular, they are suitable for use in laundry after-treatment agents which contain cationic softeners.

The present invention accordingly also relates to a detergent which is preferably in liquid form and which contains non-ionic surfactants and cationic textile softeners in addition to the novel amphoteric styrene derivatives and the conventional additives.

Suitable non-ionic surfactants are those usually encountered in commence, for example the water-soluble products which result from the addition of an alkylene oxide, or of an equivalent compound, onto a reactive hydrogen of a hydrophobic compound. The hydrophobic organic products can be heterocyclic compounds and, in particular, aliphatics or aromatics. Preferred compounds are higher aliphatic alcohols and alkylphenols, but other compounds, for example carboxylic acids, carboxamides, mercaptans, sulfamides and the like, can also be used. Preferred non-ionic compounds are the adducts of ethylene oxide with higher aliphatic alcohols having 6 to 50 C atoms or more. The amount of ethylene oxide can vary within wide limits, but, in general, at least 5 mols of ethylene oxide are required per mol of hydrophobic substance. It is possible entirely or partially to replace the ethylene oxide by other lower alkylene oxides, for example propylene oxide and butylene oxide. Other suitable non-ionic compounds which can be used are:

(a) polyoxyalkylene esters of organic acids such as higher fatty acids, resin acids, tallow oil acids and acids of petroleum oxidation products, their esters as a rule having 10 to 22 C atoms in the acid moiety and containing about 12 to about 30 mols of ethylene oxide or of its equivalent;

(b) alkylene oxide adducts of higher fatty acid amides, the fatty acid moiety as a rule having 8 to 22 C atoms and being condensed with 10 to 50 mols of ethylene oxide. The corresponding carboxamides and sulfamides can also be used as being substantially equivalent.

In the preparation of liquid concentrated detergents, the non-ionic surfactants used are preferably oxyalkylated higher aliphatic alcohols, the fatty alcohols having at least 6 and preferably at least 8 C atoms. Preferred alcohols are lauryl alcohol, myristyl alcohol, cetyl alcohol, stearyl alcohol and oleyl alcohol, which are condensed with at least 6 mols of ethylene oxide. A typical non-ionic product is the adduct of an aliphatic alcohol having 12–13 C atoms with about 6.5 mols of ethylene oxide. The corresponding alkylmercaptans, after condensation with ethylene oxide, can also be used as non-ionic surfactants.

The oxyalkylated higher aliphatic alcohols are particularly suitable for domestic detergents since they are easily biologically degradable and have good compatibility with cationic surfactants and textile softeners and with the other additives.

Particularly suitable cationic textile softeners are quaternary derivatives of ammonia and/or of imidazoline, having 2 long-chain aliphatic radicals, for example 1-methyl-1-oleylamidoethyl-2-oleyl-imidazolinium.X$^\ominus$, 1-methyl-1-tallylamidoethyl-2-tallyl-imidazolinium.X$^\ominus$, di-tallyl-dimethyl-ammonium.X$^\ominus$ and a compound of the formula

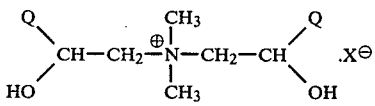

in which Q is $C_{14-16}$-alkyl and X$^\ominus$ is a chloride, bromide, methyl-sulfate, ethyl-sulfate, methanesulfonate, ethanesulfonate or toluenesulfonate anion.

The quaternary textile softeners which can be used according to the invention, and especially those mentioned above, impart a soft and fluffy handle, and at the same time good ease of remoistening, to the fabric. These textile softeners are substantive towards the fabric and contribute to reducing the electrostatic charge and reducing the tendency to crease, so that the fabric can be ironed more easily and is more pleasant to wear.

The liquid medium for the detergents according to the invention is aqueous and can consist of water alone or of water and additional solvents for certain additives. The additional solvents can account for up to 20%, preferably up to 15%, of the total amount of solvent. Suitable additional solvents are: lower alkanols or a lower diol or polyol, for example ethanol, isopropanol, ethylene glycol, propylene glycol and glycerol. Etherified polyols, such as diethylene glycol, ethylene glycol diethyl ether and ethylene glycol monoethyl ether, can also be used as additional solvents.

The liquid detergent according to the invention can contain various selected compatible additives such as soil-suspending agents or greying inhibitors, for example polyvinyl alcohol and hydroxypropylmethylcellulose; foam inhibitors; preservatives, for example sodium benzoate; UV absorbers and perfumes. Of course, these are selected so as to be compatible with the main components of the detergent.

The non-ionic surfactants are employed in amounts of 10 to 70% by weight, preferably 60% by weight. The concentration of the textile softener is 1 to 30% by weight, preferably 6 to 21% by weight. The aqueous solvent, preferably water, which can additionally contain monohydric, dihydric and polyhydric alcohols and similar solvents, is present in an amount of 5 to 60% by weight. The finished liquid or pulverulent detergent contains the compounds according to the invention in amounts of 0.005 to 3% by weight. The content of the other assistants is preferably less than 5% by weight of the detergent, since the use of larger amounts can affect the properties of liquid detergents. Although the preferred detergent preparation according to the Application is a stable clear liquid, it is possible to add a compatible clouding agent thereto in order to create an opaque appearance.

The detergent according to the invention can be used in soft or moderately hard water at elevated temperatures. This detergent can also be used for washing textiles in very hard water at lower temperatures. The water hardness can accordingly vary from 0 to more than 300 ppm, calculated as calcium carbonate, and the washing temperature can be 4° to 60° C.

The detergent according to the invention dissolves very readily in cold or warm washing water, cleans thoroughly, eliminates electrostatic charges and gives the laundry a soft handle without making it hydrophobic. The preferred detergent is in the form of a clear stable liquid which retains its activity and uniformity over prolonged periods of time. To prepare clear liquid detergents, the concentration of the active substances can only be varied within certain limits. Thus, for example, the concentration of the textile softener should not be much higher than 30% if it is desired to obtain a clear liquid detergent.

The compounds according to the invention are added in amounts of 0.005 to 1% or more, based on the weight of the finished liquid or pulverulent detergent or textile treatment agent. When used to wash textiles consisting of cellulose fibres, polyamide fibres, resin-finished cellulose fibres, polyester fibres, wool and the like, washing/treating liquors which contain the stated amounts of the claimed brighteners give textiles having a brilliant appearance in daylight.

The washing treatment is carried out, for example, as follows: the textiles mentioned are treated for 1 to 30 minutes, at 20° to 100° C., in a washing liquor which contains 0.1 to 10 g/kg of a composite detergent containing a builder, and 0.05 to 1%, based on the weight of detergent, of the claimed brighteners. The liquor ratio can be 1:3 to 1:50. After washing, the textile is rinsed and dried in the usual manner.

Under suitable washing conditions, the amphoteric carboxylic acids can also be replaced by their readily saponifiable esters, for example methyl or ethyl esters. In this way, the effects according to the invention are achieved under the conditions of the ester hydrolysis, within the practical range for washing fabrics.

In the examples, percentages are always by weight, unless stated otherwise. Melting points and boiling points are uncorrected, unless stated otherwise, and many of them are not sharp, especially in the case of the quaternised compounds.

EXAMPLE 1

5.6 g of the compound of the formula

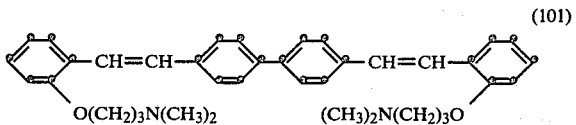

(101)

and 2.6 g of sodium chloroacetate are stirred in 50 ml of water under reflux. The pH is kept at 8–9 by periodically adding 30% aqueous sodium hydroxide solution (about 0.1 ml) dropwise. Complete dissolution takes place in the course of 3 hours. The mixture is then left to cool to room temperature and diluted with 50 ml of water, and the thickly precipitated product is filtered off with suction and washed with 10 ml of water. After drying in vacuo at 100° C., 6.8 g of a pale yellow product are obtained, which predominantly consists of the compound of the formula

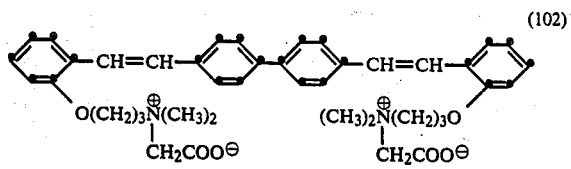
(102)

and additionally contains about 4 mols of water of crystallisation. Melting point 225° C. (not sharp), recrystallised from methanol/ethanol. The water can also be replaced by dimethyl sulfoxide as the solvent, in which case the reaction can be carried out at twice the concentration.

The crude product of the compound of the formula

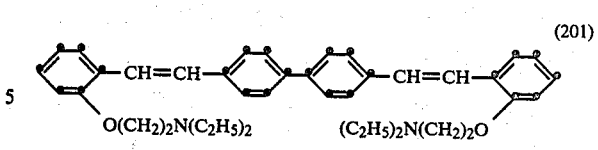
(201)

and 13.4 ml of ethyl bromoacetate in 120 ml of methyl ethyl ketone is stirred for 2 hours at the reflux temperature, the reaction product gradually separating out after a time. A sample is then soluble in water to give a clear solution. The mixture is filtered with suction at room temperature and the product is washed repeatedly with methyl ethyl ketone and dried in vacuo at 100° C. This yields 24.4 g of a light yellow product of the formula

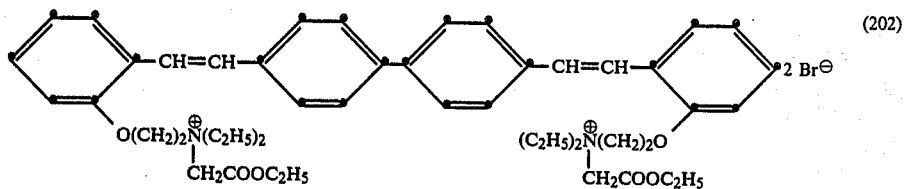
(202)

(309), which is recrystallised from ethanol (melting point 226° C.), and the crude product of the formula (215) (melting point 263° C.) are obtained similarly.

The compound of the formula

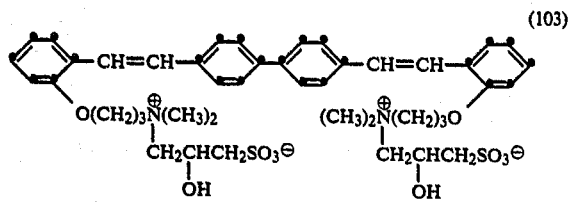
(103)

is obtained analogously from 5.6 g of the compound of the formula (101) and 6.2 g of sodium 3-chloro-2-hydroxy-propanesulfonate in 30 ml of water. Melting point 247° C. (not sharp) after recrystallisation from 3:2 n-propanol/water.

EXAMPLE 2

A solution of 17.7 g of the compound of the formula with a melting point of 159°–166° C. (unchanged after recrystallisation from isopropanol).

10.25 ml of 2N sodium hydroxide solution are rapidly added dropwise, at 90° C., with stirring, to a solution of 9.4 g of this product in 100 ml of water. The product which precipitates out during this process goes back into solution after a time. After ½ hour, the solution is diluted with about 20 ml of n-propanol and completely evaporated in vacuo on a rotary evaporator. The residue is recrystallised from methanol/ethanol, washed with ethanol and dried in vacuo at 100° C. This yields 5.6 g of the compound of the formula

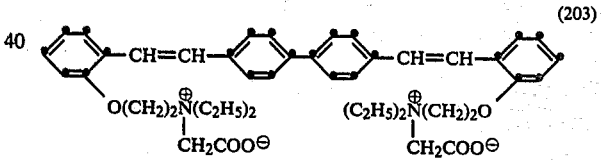
(203)

which additionally contains water of crystallisation and sodium bromide (melting point about 230° C., not at all sharp).

The quaternary esters listed in Table I, and the corresponding amphoteric carboxylic acids, are obtained analogously.

TABLE I

| Compound of the formula | R | $R_3$ | Melting point (°C.) | (crystallisable from) |
|---|---|---|---|---|
| (204) | 3-O(CH$_2$)$_2$—$\overset{\oplus}{N}$(C$_2$H$_5$)$_2$ Br$^\ominus$<br>$\mid$<br>CH$_2$COOC$_2$H$_5$ | H | 177° | |
| (205) | 3-O(CH$_2$)$_2$—$\overset{\oplus}{N}$(C$_2$H$_5$)$_2$<br>$\mid$<br>CH$_2$COO$^\ominus$ | H | 245° | (methanol/ethanol) |

TABLE I-continued

Structure: R₃, R-substituted phenyl—CH=CH—phenyl—phenyl—CH=CH—phenyl-R, R₃

| Compound of the formula | R | R₃ | Melting point (°C.) | (crystallisable from) |
|---|---|---|---|---|
| (206) | 2-O(CH₂)₃—N⊕(CH₃)₂ Br⊖ \| CH₂COOC₂H₅ | 3-OCH₃ | 151° | |
| (207) | 2-O(CH₂)₃—N⊕(CH₃)₂ \| CH₂COO⊖ | 3-OCH₃ | 272° | (methanol/ethanol) |
| (208) | 2-O(CH₂)₃—N⊕(CH₃)₂ Br⊖ \| CH₂COOC₂H₅ | 5-Cl | 184° | |
| (209) | 2-O(CH₂)₃—N⊕(CH₃)₂ \| CH₂COO⊖ | 5-Cl | 149° | (8:2 n-propanol/H₂O) |
| (210) | 2-CH₂—N⊕(CH₃)₂ Br⊖ \| CH₂COOC₂H₅ | H | 158° (decomposition) | |
| (211) | 2-CH₂—N⊕(CH₃)₂ \| CH₂—COO⊖ | H | 173° | (methanol/ethanol) |
| (212) | 2-S(CH₂)₂—N⊕(CH₃)₂ Br⊖ \| CH₂COOC₂H₅ | H | 274° | |
| (213) | 2-S(CH₂)₂—N⊕(CH₃)₂ \| CH₂COO⊖ | H | 237° | (4:1 n-propanol/H₂O) |
| (214) | 2-SO₂NH(CH₂)₃—N⊕(CH₃)₂ Br⊖ \| CH₂COOC₂H₅ | H | 200° (decomposition) | |
| (215) | 2-SO₂NH(CH₂)₃N⊕(CH₃)₂ \| CH₂COO⊖ | H | 264° (decomposition) | |
| (216) | 2-COO(CH₂)₂—N⊕(CH₃)₂ \| CH₂COOC₂H₅ | H | 260° | |
| (217) | 2-COO(CH₂)₂—N⊕(CH₃)₂ \| CH₂COO⊖ | H | 222° | (7:3 n-propanol/H₂O) |
| (218) | 2-CONH(CH₂)₃—N⊕(CH₃)₂ \| CH₂COOC₂H₅ | H | 148° (decomposition) | |
| (219) | 2-CONH(CH₂)₃—N⊕(CH₃)₂ \| CH₂COO⊖ | H | 298° (decomposition) | (8:2 n-propanol/H₂O) |

The intermediate of the formula

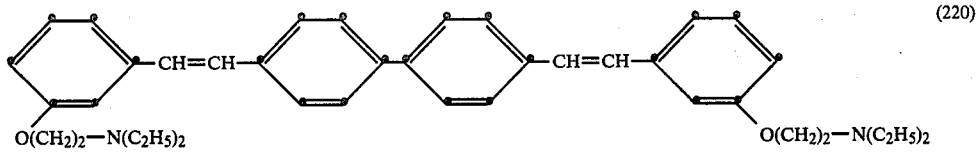
(220)

which is required for the preparation of the compound of the formula (204) is obtained, for example, as follows: 9.0 g of potassium t-butylate are added to a solution of 3.6 g of 4,4'-dimethyl-biphenyl and 12.4 g of the compound of the formula

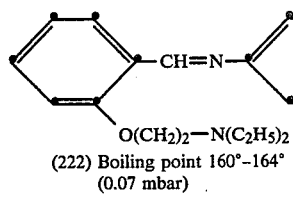

(221)

The mixture is stirred under nitrogen and the temperature is brought to 60° C. in the course of about 30 minutes, a violet colouration appearing. After subsequent stirring for 1 hour at 80° C., the mixture is left to cool and treated with 50 ml of water. The product which has precipitated out is filtered off with suction, washed repeatedly with methanol and water until the washings are neutral, and dried in vacuo at 100° C. This yields 9.0 g of the compound of the formula (220), which is recrystallised from nonane: pale yellow crystals, melting point 174°–175° C.

To prepare the anil of the formula (221), 120.3 g of 3-diethylaminoethoxybenzaldehyde (content 92%) are warmed with 48.9 g of aniline for 30 minutes at 100° C., and the water formed is distilled off, first at normal pressure and then under reduced pressure. The residue is then subjected to fractional distillation under a high vacuum. After a small amount of first runnings has been separated off, 138.0 g of a pale yellowish oil having a boiling point of 160°–164° C. (0.1 mbar) are obtained.

The corresponding anils of the formulae

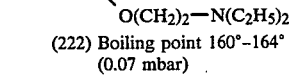

(222) Boiling point 160°–164° (0.07 mbar)

(223) Boiling point 170°– 179° (0.1 mbar)

are obtained analogously, and these are similarly reacted with 4,4'-dimethyl-biphenyl. This yields, for example, the compound of the formula (201), having a melting point of 126°–127° C., with a yield of 87% of theory. These starting materials can also be replaced by the corresponding o- or p-chloroanils or p-xylene. Other bases, such as potassium hydroxide or sodium methylate, are also suitable as catalysts.

EXAMPLE 3

16.8 g of the compound of the formula (101) are stirred in 30 ml of ethyl chloroacetate, at 70°–100° C., until the bulk of the reaction product has precipitated out. The suspension, which has become thick, is diluted with 70 ml of methyl ethyl ketone and the subsequent procedure is as described in Example 2. This yields 23.5 g of an almost colourless product of the formula

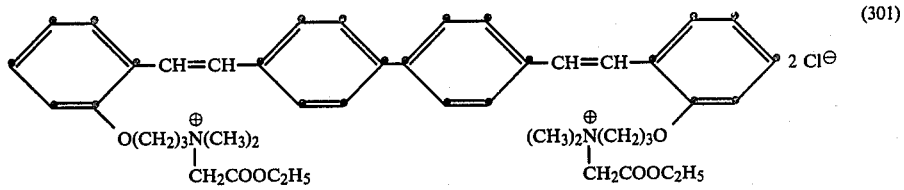

(301)

which is recrystallised from ethanol (melting point 225°–230° C.).

12.5 g of this compound are treated with sodium hydroxide solution according to Example 2, and the resulting residue is recrystallised from ethanol. This yields 8.2 g of a light yellow product of the formula (102), which still contains about 6% of sodium chloride (melting point about 230° C., not sharp).

If, in place of the starting materials indicated in this example, 17.7 g of the compound of the formula (201) are heated with 60 ml of ethyl 4-bromo-butyrate for 3 hours at 110° C., and the procedure is otherwise as described above, the compound of the formula

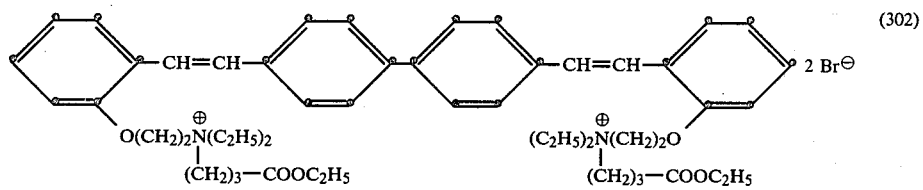

(302)

melting point 120°–140° C., is obtained, and from this the compound of the formula

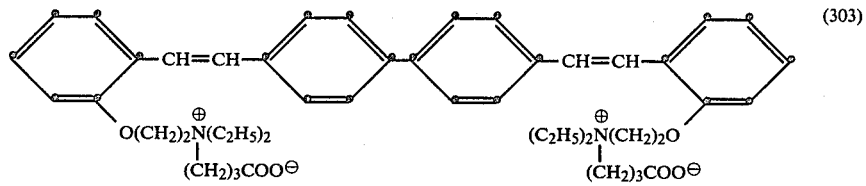

(303)

melting point 150° C. (not sharp), is obtained, which still contains sodium bromide.

The esters listed in Table II, and the corresponding amphoteric carboxylic acids, are obtained analogously.

TABLE II

| Compound of the formula | n | R | Melting point in °C. | (Recrystalised from) |
|---|---|---|---|---|
| (304) | 2 | $-O(CH_2)_2-\overset{\oplus}{N}(C_2H_5)_2$ $Cl^{\ominus}$<br>$\quad\quad\quad\quad\quad\; \mid$<br>$\quad\quad\quad\quad\;\; CH_2COOC_2H_5$ | 179° | |
| (305) | 1 | $-O(CH_2)_2-\overset{\oplus}{N}(C_2H_5)_2$ $Cl^{\ominus}$<br>$\quad\quad\quad\quad\quad\; \mid$<br>$\quad\quad\quad\quad\;\; CH_2COOC_2H_5$ | about 170° (decomposition) | |
| (306) | 1 | $-O(CH_2)_2-\overset{\oplus}{N}(C_2H_5)_2$ $Cl^{\ominus}$<br>$\quad\quad\quad\quad\quad\; \mid$<br>$\quad\quad\quad\quad\;\; CH_2COOCH_3$ | about 136° (decomposition) hygroscopic | |
| (307) | 1 | $-O(CH_2)_2-\overset{\oplus}{N}(C_2H_5)_2$<br>$\quad\quad\quad\quad\quad\; \mid$<br>$\quad\quad\quad\quad\;\; CH_2COO^{\ominus}$ | about 230° | (n-propanol) |
| (308) | 1 | $-O(CH_2)_3-\overset{\oplus}{N}(CH_3)_2$ $Cl^{\ominus}$<br>$\quad\quad\quad\quad\quad\; \mid$<br>$\quad\quad\quad\quad\;\; CH_2COOC_2H_5$ | about 220° (decomposition) | |
| (309) | 1 | $-O(CH_2)_3-\overset{\oplus}{N}(CH_3)_2$<br>$\quad\quad\quad\quad\quad\; \mid$<br>$\quad\quad\quad\quad\;\; CH_2COO^{\ominus}$ | about 240° | (n-propanol) |
| (310) | 1 | $-O(CH_2)_2-\overset{\oplus}{N}(C_2H_5)_2$ $Br^{\ominus}$<br>$\quad\quad\quad\quad\quad\; \mid$<br>$\quad\quad\quad\quad\;\; (CH_2)_3-COOC_2H_5$ | about 152° | (1,2-dichloroethane) |
| (311) | 1 | $-O(CH_2)_2-\overset{\oplus}{N}(C_2H_5)_2$<br>$\quad\quad\quad\quad\quad\; \mid$<br>$\quad\quad\quad\quad\;\; (CH_2)_3-COO^{\ominus}$ | about 203° | (n-propanol) |

TABLE II-continued

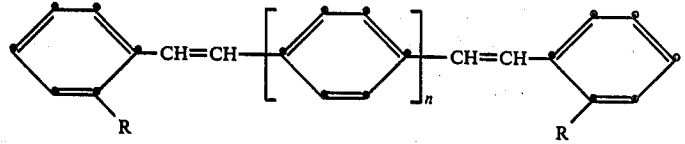

| Compound of the formula | n | R | Melting point in °C. | (Recrystalised from) |
|---|---|---|---|---|
| (312) | 2 | 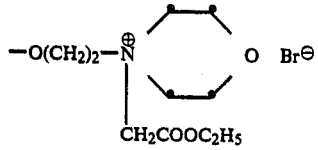 | about 200° | |
| (313) | 2 | 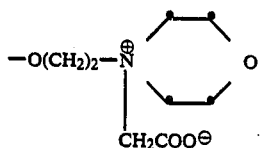 | 267° | (7:3 n-propanol/$H_2O$) |

EXAMPLE 4

A solution of 15.4 g of the compound of the formula

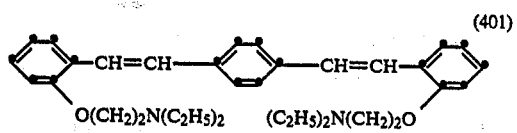

is quaternised with 13.4 ml of ethyl bromoacetate according to Example 2. This yields 24.2 g of the compound of the formula

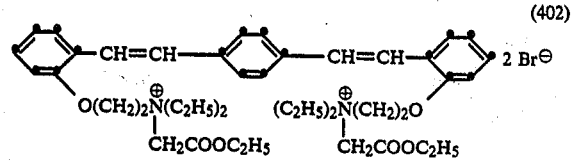

as a light yellow product having a melting point of 176°–180° C., which still contains ½ mol of water of crystallisation.

12.8 g of this compound are saponified with sodium hydroxide solution as described in Example 2. The evaporation residue is extracted by boiling with 200 ml of acetone, and the resulting suspension is filtered with suction at room temperature. After the residue has been rinsed with acetone and dried in vacuo at 100° C., 9.7 g of the compound of the formula

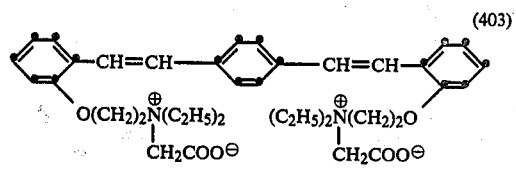

are obtained as a light yellow powder having a melting point of 225° C. (not sharp), which contains about 23% of sodium bromide.

The quaternised esters listed in Table III, and the corresponding amphoteric carboxylic acids, are obtained analogously:

TABLE III

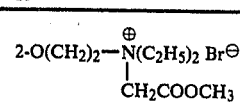

| Compound of the formula | R | $R_3$ | Melting point (°C.) (recrystallised from) |
|---|---|---|---|
| (404) | 2-O($CH_2$)$_2$—$\overset{\oplus}{N}$($C_2H_5$)$_2$ Br$^\ominus$<br>\|<br>$CH_2COOCH_3$ | H | 174° (decomposition) |
| (405) | 2-O($CH_2$)$_3$—$\overset{\oplus}{N}$($CH_3$)$_2$ Br$^\ominus$<br>\|<br>$CH_2COOC_2H_5$ | 5-$CH_3$ | 189° (decomposition) |

TABLE III-continued

[Structure: R₃ and R substituted triphenyl with two CH=CH linkages]

| Compound of the formula | R | R₃ | Melting point (°C.) (recrystallised from) |
|---|---|---|---|
| (406) | 2-O(CH₃)₃—N⁺(CH₃)₂ \| CH₂COO⁻ | 5-CH₃ | 152° (n-propanol) |
| (407) | 2-O(CH₂)₂—N⁺(piperidine ring) Br⁻ \| CH₂COOC₂H₅ | H | 146° |
| (408) | 2-O(CH₂)₂—N⁺(piperidine ring) \| CH₂COO⁻ | H | 129° (isopropanol) |

EXAMPLE 5

5.9 g of 1,3-propanesultone are added dropwise at the reflux temperature, with stirring, to a solution of 11.2 g of the compound of the formula (101) in 50 ml of methyl ethyl ketone, after which the reaction product gradually separates out. After 2 hours have elapsed, the mixture is cooled and filtered with suction and the residue is repeatedly washed with methyl ethyl ketone and dried in vacuo at 100° C. This yields 15.5 g of a light yellow product of the formula

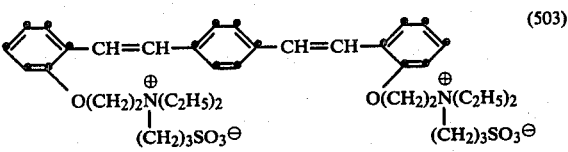
(503)

which contains 1 mol of water of crystallisation (melting point 235° C., not sharp), is obtained analogously.

EXAMPLE 6

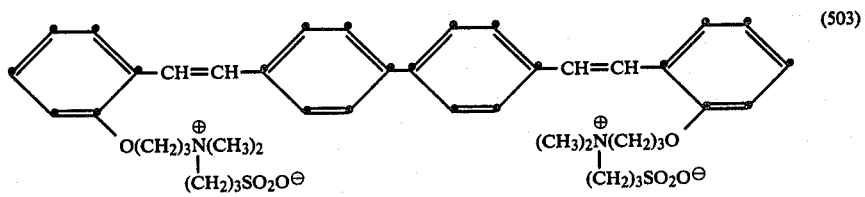
(503)

which contains ½ mol of water of crystallisation. Melting point 298°–303° C. (decomposition).

If the 1,3-propanesultone is replaced by 6.5 g of 1,4-butanesultone, the compound of the formula

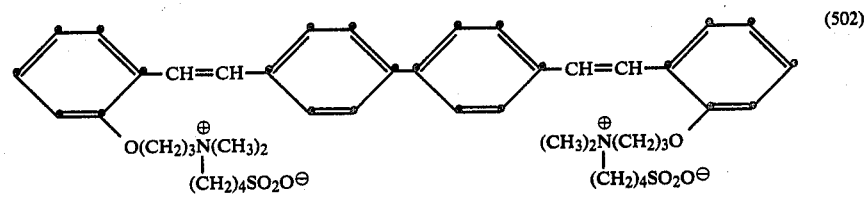
(502)

melting point 244°–248° C. (decomposition), is obtained after extraction with boiling water, evaporation of the aqueous solution and crystallisation of the residue from ethanol.

The compound of the formula

After displacement of the air by nitrogen, 8.9 g of a 30.5% methanolic sodium methylate solution are added dropwise, with stirring, to a mixture of 3.8 g of 1,4-bis-(diethoxyphosphonomethyl)-benzene and 6.2 g of the compound of the formula

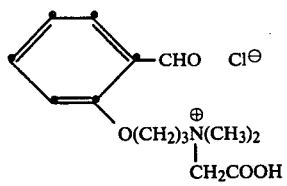

(601)

in 30 ml of dimethylformamide, in such a way that the temperature does not exceed 40° C. The temperature is kept at 40°-45° C. for 2 hours, the mixture is neutralised to pH 7 with aqueous hydrochloric acid and the solution is completely evaporated in vacuo on a rotary evaporator. The residue is boiled in 40 ml of isopropanol, filtered off after cooling in an ice bath, washed with isopropanol and dried. The resulting product is recrystallised from n-propanol in order to remove the bulk of the sodium chloride. This yields 2.6 g of the compound of the formula (309).

The compound of the formula (601) can be prepared as follows:

11.7 ml of ethyl chloroacetate are added dropwise, at the reflux temperature, to a solution of 26.2 g of 2-(3-dimethylaminopropoxy)-benzaldehyde in 100 ml of ethyl methyl ketone. After stirring for 1 hour at the reflux temperature, the mixture is left to cool and the product which has separated out is filtered off with suction, washed repeatedly with ethyl methyl ketone and dried in vacuo at 60° C. This yields 25.8 g of the compound of the formula (602)

in the form of colourless crystals having a melting point of 190°-193° C.

11.9 g of this product are stirred for 1 hour, at the reflux temperature, in 12.7 ml of water and 7.3 g of 36% hydrochloric acid. The resulting solution is completely evaporated in vacuo on a rotary evaporator and the residue is dissolved in 50 ml of hot n-propanol. On cooling, the reaction product precipitates out as colourless crystals. This product is filtered off with suction at 0° C., washed repeatedly with n-propanol and dried in vacuo at 100° C. This yields 7.9 g of the compound (601) having a melting point of 200°-203° C.

EXAMPLE 7

14.0 g of the compound of the formula (101) are stirred in 15 ml of 1,3-dichloro-2-propanol for about 3 hours at 90°-100° C. The resulting solution is treated with 250 ml of methyl ethyl ketone, the reaction product precipitating out. This is filtered off with suction at room temperature, washed repeatedly with methyl ethyl ketone and dried in vacuo at 50° C. This yields 18.0 g of the compound of the formula

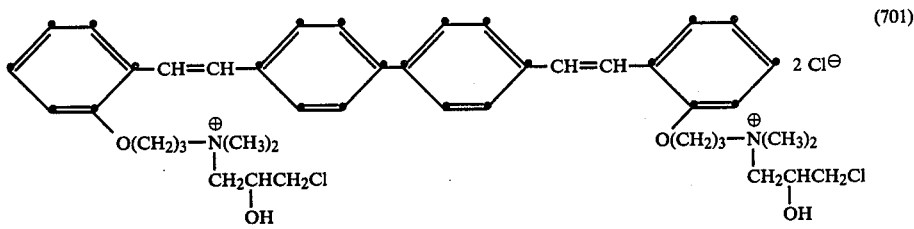

(701)

melting point about 155° C. (decomposition).

8.2 g of this product and 3.2 g of 96% pure sodium sulfite are stirred overnight, at the reflux temperature, in 50 ml of water and 15 ml of n-propanol. The product which has precipitated out after cooling is filtered off with suction, washed with ice-water and dried in vacuo at 100° C. This yields 7.4 g of crude product of the compound of the formula (103).

EXAMPLE 8

A mixture of 5.1 g of the compound of the formula (401), 4 ml of ethanol and 2.35 ml of ethyl bromoacetate is heated to the reflux temperature (82° C.), with stirring, dissolution taking place. After one hour has elapsed, the quaternisation has ended, i.e. a sample is soluble in water to give a clear solution and shows no further starting material on a thin layer chromatogram. 10.5 ml of 2N sodium hydroxide solution are then added dropwise in the course of about 5 minutes, stirring is continued at the reflux temperature until the solution has become almost neutral (about 1 hour), and the solution is left to cool. This yields a stable aqueous solution of the compound of the formula (403) with a content of 27.2%, which still contains some alcohol, sodium bromide and glycolic acid (partially as the sodium salt).

If, in this example, corresponding amounts of methyl bromoacetate and methanol are used, the methanol is distilled off after addition of the sodium hydroxide solution, and the pH is adjusted to 8 with 0.1 ml of concentrated ammonia solution, the procedure otherwise being the same, a corresponding aqueous solution of the compound of the formula (403) is obtained.

EXAMPLE 9

The compounds listed in Tables IV and V are obtained in a similar manner to that described in the previous examples.

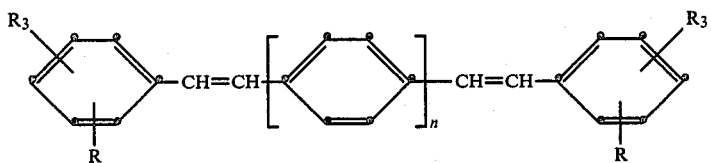

TABLE IV

| Compound No. | R | R₃ | n | Fluorescence |
|---|---|---|---|---|
| (901) | 2-O(CH$_2$)$_2$N$^⊕$(CH$_3$)$_2$ / CH$_2$COO$^⊖$ | H | 2 | blue |
| (902) | 2-O(CH$_2$)$_2$—N$^⊕$(7-membered ring) / CH$_2$COO$^⊖$ | H | 2 | " |
| (903) | 2-O(CH$_2$)$_2$—N$^⊕$(6-membered ring) / CH$_2$COO$^⊖$ | H | 2 | " |
| (904) | 2-O(CH$_2$)$_2$—N$^⊕$(5-membered ring) / CH$_2$COO$^⊖$ | H | 2 | " |
| (905) | 2-O(CH$_2$)$_3$—N$^⊕$(CH$_3$)$_2$ / CH$_2$COO$^⊖$ | 5-CH$_3$ | 2 | greenish-blue |
| (906) | 3-O(CH$_2$)$_3$—N$^⊕$(CH$_3$)$_2$ / CH$_2$COO$^⊖$ | H | 2 | violet-blue |
| (907) | 2-OCHCH$_2$—N$^⊕$(CH$_3$)$_2$ / CH$_3$    CH$_2$COO$^⊖$ | mixture | 2 | blue |
| (908) | 2-OCH$_2$CH—N$^⊕$(CH$_3$)$_2$ / CH$_3$    CH$_2$COO$^⊖$ | H | | |
| (909) | 2-OCH$_2$CHCH$_2$—N$^⊕$(CH$_3$)$_2$ / OH    CH$_2$COO$^⊖$ | H | 2 | " |
| (910) | 2-O(CH$_2$)$_3$—N$^⊕$(CH$_3$)$_2$ / H$_3$C—CH—COO$^⊖$ | H | 2 | " |
| (911) | 2-O(CH$_2$)$_3$—N$^⊕$(CH$_3$)$_2$ / (CH$_2$)$_3$COO$^⊖$ | H | 2 | " |
| (912) | 2-O(CH$_2$)$_2$—N$^⊕$(C$_2$H$_5$)$_2$ / (CH$_2$)$_3$SO$_3$$^⊖$ | H | 2 | " |

TABLE IV-continued

| Compound No. | R | R₃ | n | Fluorescence |
|---|---|---|---|---|
| (913) | 3-O(CH$_2$)$_2$—$\overset{\oplus}{N}$(C$_2$H$_5$)$_2$ / (CH$_2$)$_3$SO$_3^\ominus$ | H | 2 | " |
| (914) | 2-O(CH$_2$)$_2$—$\overset{\oplus}{N}$(C$_2$H$_5$)$_2$ / CH$_2$CHCH$_2$SO$_3^\ominus$ / OH | H | 2 | " |
| (915) | 3-SO$_2$NH(CH$_2$)$_3$—$\overset{\oplus}{N}$(CH$_3$)$_2$ / CH$_2$COO$^\ominus$ | H | 2 | " |
| (916) | 3-COO(CH$_2$)$_3$—$\overset{\oplus}{N}$(CH$_3$)$_2$ / CH$_2$COO$^\ominus$ | H | 2 | " |
| (917) | 3-COO(CH$_2$)$_2$—$\overset{\oplus}{N}$(CH$_3$)$_2$ / CH$_2$—COO$^\ominus$ | 6-CH$_3$ | 2 | " |
| (918) | 2-SO$_2$—N(CH$_2$CH$_2$CN)—(CH$_2$)$_3$—$\overset{\oplus}{N}$—(CH$_3$)$_2$ / CH$_2$COO$^\ominus$ | H | 2 | green-blue |
| (919) | 2-SO$_2$NH(CH$_2$)$_3$—$\overset{\oplus}{N}$(CH$_3$)$_2$ / (CH$_2$)$_3$SO$_3^\ominus$ | H | 2 | " |
| (920) | 2-SO$_2$—N⌒$\overset{\oplus}{N}$—CH$_3$ / CH$_2$COO$^\ominus$ | H | 2 | " |
| (921) | 4-O(CH$_2$)$_3$—$\overset{\oplus}{N}$(CH$_3$)$_2$ / CH$_2$COO$^\ominus$ | H | 1 | " |
| (922) | 2-O(CH$_2$)$_2$—$\overset{\oplus}{N}$(CH$_3$)$_2$ / CH$_2$COO$^\ominus$ | H | 1 | blue |
| (923) | 2-O(CH$_2$)$_2$—$\overset{\oplus}{N}$(C$_2$H$_5$)$_2$ / CH$_2$COO$^\ominus$ | 5-t-C$_4$H$_9$ | 1 | greenish-blue |
| (924) | 2-O(CH$_2$)$_2$—$\overset{\oplus}{N}$(C$_2$H$_5$)$_2$ / CH$_2$COO$^\ominus$ | 3-CH$_3$ | 1 | blue |
| (925) | 2-O(CH$_2$)$_2$—$\overset{\oplus}{N}$(C$_2$H$_5$)$_2$ / CH$_2$COO$^\ominus$ | 4-CH$_3$ | 1 | greenish-blue |
| (926) | 3-O(CH$_2$)$_2$—$\overset{\oplus}{N}$(C$_2$H$_5$)$_2$ / CH$_2$COO$^\ominus$ | 2-Cl | 1 | blue |
| (927) | 2-O(CH$_2$)$_2$—$\overset{\oplus}{N}$(C$_2$H$_5$)$_2$ / CH$_2$COO$^\ominus$ | 3-Cl | 1 | " |

TABLE IV-continued

| Compound No. | R | $R_3$ | n | Fluorescence |
|---|---|---|---|---|
| (928) | 4-O(CH$_2$)$_2$—N$^{\oplus}$(C$_2$H$_5$)$_2$ \| CH$_2$COO$^{\ominus}$ | 2-Cl | 1 | greenish-blue |
| (929) | 2-O(CH$_2$)$_2$—N$^{\oplus}$(morpholino) \| CH$_2$COO$^{\ominus}$ | H | 1 | blue |
| (930) | 2-O(CH$_2$)$_2$—N$^{\oplus}$(cycloheptyl) \| CH$_2$COO$^{\ominus}$ | H | 1 | " |
| (931) | 2-O(CH$_2$)$_2$—N$^{\oplus}$(pyrrolidino) \| CH$_2$COO$^{\ominus}$ | H | 1 | " |
| (932) | 3-SO$_2$NH(CH$_2$)$_3$—N$^{\oplus}$(CH$_3$)$_2$ \| CH$_2$COO$^{\ominus}$ | 4-Cl | 1 | " |
| (933) | 2-O(CH$_2$)$_2$—N$^{\oplus}$(C$_2$H$_5$)$_2$ \| (CH$_2$)$_3$SO$_3$$^{\ominus}$ | H | 1 | " |
| (934) | 2-O(CH$_2$)$_2$—N$^{\oplus}$(C$_2$H$_5$)$_2$ \| (CH$_2$)$_3$SO$_3$$^{\ominus}$ | H | 1 | " |
| (935) | 2-O(CH$_2$)$_3$—N$^{\oplus}$(CH$_3$)$_2$ \| (CH$_2$)$_4$SO$_3$$^{\ominus}$ | H | 1 | " |
| (936) | 2-O(CH$_2$)$_3$—N$^{\oplus}$(CH$_3$)$_2$ \| CH$_2$CHCH$_2$SO$_3$$^{\ominus}$ \| OH | H | 1 | " |
| (937) | 2-OCH$_2$CHCH$_2$—N$^{\oplus}$—(CH$_3$)$_2$ \| OH \| CH$_2$COO$^{\ominus}$ | H | 1 | " |
| (938) | 2-O(CH$_2$)$_2$—N$^{\oplus}$(C$_2$H$_5$)$_2$ \| CH$_2$COO$^{\ominus}$ | 3-CH$_2$CH=CH$_2$ | 1 | " |
| (939) | 4-CH$_2$N$^{\oplus}$(CH$_3$)$_2$ \| CH$_2$COO$^{\ominus}$ | H | 2 | " |
| (940) | 3-O(CH$_2$)$_2$—N$^{\oplus}$(C$_2$H$_5$)$_2$ \| CH$_2$COO$^{\ominus}$ | 2-Cl | 1 | " |
| (941) | 3-COO(CH$_2$)$_2$—N$^{\oplus}$(CH$_3$)$_2$ \| CH$_2$COO$^{\ominus}$ | 6-CH$_3$ | 1 | " |

TABLE IV-continued

| Compound No. | R | R$_3$ | n | Fluorescence |
|---|---|---|---|---|
| (942) | 2-CONH(CH$_2$)$_3$—$\overset{\oplus}{\text{N}}$(CH$_3$)$_2$<br>$\mid$<br>CH$_2$COO$^\ominus$ | H | 1 | " |
| (943) | 3-CONH(CH$_2$)$_3$—$\overset{\oplus}{\text{N}}$(CH$_3$)$_2$<br>$\mid$<br>CH$_2$COO$^\ominus$ | 6-CH$_3$ | 1 | blue-violet |

TABLE V $$\underset{R_4 \quad R}{\overset{R_3}{\diagdown}}\!\!-\!\!CH\!=\!CH\!-\!\!\diagup\!\!-\!\!CH\!=\!CH\!-\!\!\underset{R \quad R_4}{\overset{R_3}{\diagup}}$$

| Compound No. | R | R$_3$ | R$_4$ | Fluorescence |
|---|---|---|---|---|
| (944) | 2-O(CH$_2$)$_2$—$\overset{\oplus}{\text{N}}$(C$_2$H$_5$)$_2$<br>$\mid$<br>CH$_2$COO$^\ominus$ | 3-CH$_3$ | 5-CH$_3$ | blue |
| (945) | 2-O(CH$_2$)$_2$—$\overset{\oplus}{\text{N}}$(C$_2$H$_5$)$_2$<br>$\mid$<br>CH$_2$COO$^\ominus$ | 4,5-(CH$_2$)$_3$ | | greenish-blue |
| (946) | 2-O(CH$_2$)$_2$—$\overset{\oplus}{\text{N}}$(C$_2$H$_5$)$_2$<br>$\mid$<br>CH$_2$COO$^\ominus$ | 4,5-(CH$_2$)$_4$ | | greenish-blue |
| (947) | 2-O(CH$_2$)$_2$—$\overset{\oplus}{\text{N}}$(C$_2$H$_5$)$_2$<br>$\mid$<br>CH$_2$COO$^\ominus$ | 3-Cl | 5-Cl | greenish-blue |
| (948) | 4-O(CH$_2$)$_2$—$\overset{\oplus}{\text{N}}$(C$_2$H$_5$)$_2$<br>$\mid$<br>CH$_2$COO$^\ominus$ | 2-CH$_3$ | 5-CH$\diagup$CH$_3$$\diagdown$CH$_3$ | greenish-blue |
| (949) | 2-O(CH$_2$)$_2$—$\overset{\oplus}{\text{N}}$(C$_2$H$_5$)$_2$<br>$\mid$<br>CH$_2$COO$^\ominus$ | 4-CH$_3$ | 5-Cl | greenish-blue |

EXAMPLE 10

A bleached cotton fabric is washed for 15 minutes, at a liquor ratio of 1:30, in a warm aqueous liquor at 40° C., which contains, per liter, 0.4 g of soil corresponding to known skin grease ("Spangler Soil"), 1.5 g of a liquid detergent (a), (b) or (c) and 0.1% of a brightener of the formula (102), (203), (219), (307), (309), (313) or (403) based on the detergent. The cotton fabric is then rinsed for 20 seconds in running drinking water and dried at 70° C. in a drying cabinet. The fabric treated in this way shows just as strong a white effect as a fabric which is washed without this added soil, even after the washing process has been repeated 5 to 10 times.

"Spangler Soil" consists of a mixture of various fatty acids, esters, fats, oils and the like, cf. W. G. Spangler et al., "A laboratory method for testing laundry products for detergency", J. Am. Oil. Chem. Soc., 42, 723–727 (1965). The soil is incorporated via the liquid detergent, before dilution with water.

The liquid detergent used is prepared by mixing the following components (% by weight):

| | |
|---|---|
| (a) Oxyethyleneated alcohols (C$_{11-12}$-alcohols with 5–6 mols of ethylene oxide) | 64% |
| 1-Methyl-1-oleyamidoethyl-2-oleyl-imidazolinium methosulfate | 20% |
| Water | 13% |
| Customary additive | 3% |
| (b) Oxyethyleneated alcohols (C$_{12-13}$-alcohols with 6.5 mols of ethylene oxide) | 55% |
| 1-Methyl-1-tallylamidoethyl-2-tallyl-imidazolinium methosulfate | 26% |
| Water | 13% |
| Isopropanol | 5% |
| Customary additives | 1% |
| (c) Oxyethyleneated alcohols (C$_{14-15}$-alcohols with 7 mols of ethylene oxide) | 12.0% |
| Oxyethyleneated alcohols (C$_{12-13}$-alcohols with 6.5 mols of ethylene oxide) | 12.0% |
| non-cured di-tallyl-dimethyl-ammonium chloride | 6.4% |
| Ethanol | 15.0% |
| Sodium bicarbonate | 0.3% |
| Customary additives | 0.6% |
| Water | 53.7% |

EXAMPLE 11

A bleached cotton fabric is padded with a liquor which contains 1 g/liter of the brightener of the formula (307), (309), (403) or (408), 1 g/liter of an adduct of 1 mol of stearyl alcohol and 35 mols of ethylene oxide, 1 g/liter of an adduct of 1 mol of p-tert.-octylphenol and 8 mols of ethylene oxide, 90 ml of ethanol (95%) and 2 g/liter of sodium tripolyphosphate. The fabric is squeezed off to a liquor uptake of 75%. The fabric treated in this way is then placed in a dyeing apparatus which contains an amount of water such that the liquor ratio is 1:25. The application then takes place according to the following temperature program:

30°–70° C./10 minutes
70° C./20 minutes.

The fabric is then rinsed in cold softened water, spun and dried with a warm iron at 155° C. The cotton fabric treated in this way shows a good white effect.

EXAMPLE 12

A polyacrylonitrile fabric (Orlon 75) is treated in a dyeing apparatus, at a liquor ratio of 1:20, with an aqueous liquor which contains 0.1% of the brightener of the formula (209), (307), (309), (313), (406) or (408), based on the weight of goods, 1 g/liter of an adduct of 35 mols of ethylene oxide and 1 mol of stearyl alcohol, and 1.5 ml/liter of 85% formic acid.

The application takes place according to the following temperature program:
40°–97° C./30 minutes
97° C./30 minutes
97°–40° C./15 minutes.

The polyacrylonitrile fabric is then rinsed for 20 seconds in running softened water and dried at 70° C. in a drying cabinet. The fabric treated in this way shows a good white effect.

EXAMPLE 13

A bleached cotton fabric is treated for 15 minutes, at a liquor ratio of 1:20, in a warm aqueous soft-rinse liquor at 30° C., which contains, per liter,
0.2 g of quaternary dimethyldistearylammonium chloride and
0.01 g of the brightener of the formula (102), (203), (219), (307), (309), (313) or (403).

The cotton fabric is then rinsed for 5 seconds in running drinking water and dried at 70° C. in a drying cabinet. The cotton fabric treated in this way shows a good white effect.

EXAMPLE 14

A bleached cotton fabric is washed for 15 minutes at a liquor ratio of 1:20, in a 40° C. warm aqueous liquor, which contains, per liter,
0.5 g of an adduct of 10 mols of ethylene oxide and one mol of stearyl alcohol, and
0.01 g of the brightener of the formula (102), (203), (219), (307), (309), (313) or (403).

The cotton fabric is then rinsed for 20 seconds in running drinking water and dried at 70° C. in a drying cabinet. The cotton fabric treated in this way shows a good white effect.

If 0.2 g/liter of active chlorine, in the form of sodium hypochlorite, is also added to the previously described liquor, and the procedure is as described, equally good white effects are obtained.

EXAMPLE 15

0.3 g of the brightener of the formula (102), (207), (209), (211), (213), (313) or (406) is dissolved in 270 ml of softened water, which contain 0.27 g of acetic acid (80%). 0.3 g of the adduct of 35 mols of ethylene oxide and 1 mol of stearyl alcohol, 0.3 g of the adduct of 8–9 mols of ethylene oxide and 1 mol of p-tert.-octylphenol, and 30 ml of ethanol (95%) are added to this solution. 9 g of heavy polyamide fabric are introduced into this brightener solution, warmed to 50° C. The temperature is raised to 100° C. within 10 minutes and the solution is left at this temperature for 20 minutes and then cooled to 50° C. within 5 minutes. The fabric is then rinsed in softened water, spun and dried with an iron at 180° C. The fabric treated in this way shows a good white effect.

EXAMPLE 16

5 g of fibrous material (consisting of bleached sulfite pulp and bleached beech pulp in a ratio of 1:1), in 150 ml of water containing 5 mg of a cationic polyether amine, are mixed in a mixer, for 15 minutes, with 50 ml of a brightener solution containing 4 mg, corresponding to a concentration of 0.08%, of the brightener of the formula (102), (203), (307) or (309). 1.5% by weight of size, for example Bewoidleim ®, 2.5% by weight of aluminium sulfate and 0.1% of a cationic polyether amine (based on the dry weight of fibre) are then added and the mixture is diluted to 1,000 ml with water of about 10° of hardness. This fibre suspension is used to form a sheet of paper which shows a good white effect.

EXAMPLE 17

5 g of fibrous material (consisting of bleached sulfite pulp and bleached beech pulp in a ratio of 1:1), in 150 ml of water containing 5 mg of a polyethyleneimine, are mixed in a mixer, for 15 minutes, with 50 ml of a brightener solution containing 4 mg, corresponding to a concentration of 0.08%, of the brightener of the formula (102), (203), (307) or (309). 1.5% by weight of size, for example Bewoidleim ®, 2.5% by weight of aluminium sulfate and 0.1% of a polyethyleneimine (based on the dry weight of fibre) are then added and the mixture is diluted to 1,000 ml with water of about 10° of hardness. This fibre suspension is used to form a sheet of paper which shows a good white effect.

EXAMPLE 18

A fabric consisting of bleached wool is padded with a liquor which contains 0.05% of the brightener of the formula (102), (403), (406) or (501), based on the weight of the fabric, 1 g/liter of the adduct of 35 mols of ethylene oxide and 1 mol of stearyl alcohol, 1 g/liter of the adduct of 8–9 mols of ethylene oxide and 1 mol of 4-isooctylphenol, and 1 ml/liter of acetic acid (80%). The fabric is squeezed off to a liquor uptake of 70%. The fabric treated in this way is then placed in a dyeing apparatus which contains water in an amount such that the liquor ratio is 1:25. The application then takes place according to the following temperature program:
30°–60° C./10 minutes
60° C./75 minutes.

The fabric is then rinsed in cold softened water, spun and dried with a warm iron at 155° C. The wool fabric treated in this way shows a good white effect.

What is claimed is:

1. An amphoteric styrene derivative of the formula

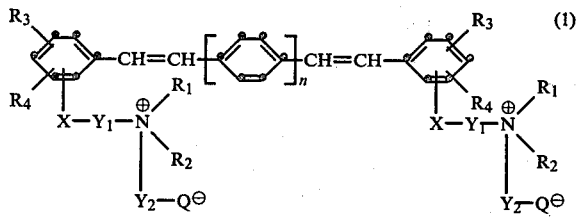

in which X is oxygen, sulfur, a direct bond, $-SO_2N(R_5)-$, $-CON(R_5)-$ or $-COO-$, $Y_1$ and $Y_2$ independently of one another are $C_1$–$C_4$-alkylene or hydroxypropylene, $R_1$ and $R_2$ independently of one another are $C_1$–$C_4$-alkyl or, together with the N atom, are a pyrrolidine, piperidine, hexamethyleneimine or morpholine ring, and $R_1$, together with $R_5$, is also a piperazine ring, $R_3$ and $R_4$ are hydrogen, $C_{1-4}$-alkyl, chlorine, $C_{1-4}$-alkoxy or $C_{3-4}$-alkenyl or together, in the o-position relative to one another, are a trimethylene or tetramethylene group, $R_5$ is hydrogen, $C_{1-4}$-alkyl or cyanoethyl or, together with $R_1$, is a piperazine ring, Q is $-COO$ or $-SO_3$ and n is the number 1 or 2.

2. An amphoteric styrene derivative according to claim 1, of the formula

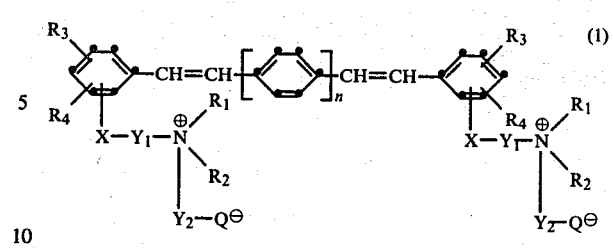

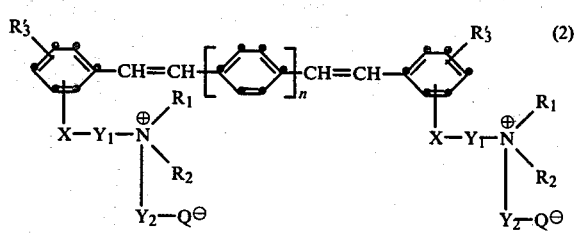

in which $R_1$, $R_2$, $Y_1$, $Y_2$, Q and n are as defined in claim 1, $X_1$ is oxygen, a direct bond, —CONH— or —COO— and $R'_3$ is hydrogen, $C_{1-4}$-alkyl, methoxy or chlorine.

3. An amphoteric styrene derivative according to claim 2, of the formula

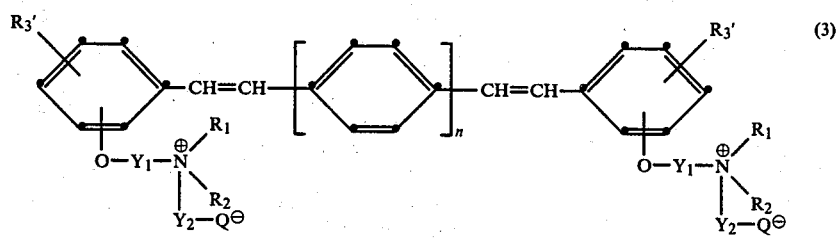

in which $R_1$, $R_2$, $R'_3$, $Y_1$, $Y_2$, Q and n are as defined in claim 2.

4. An amphoteric styrene derivative according to claim 3, of the formula

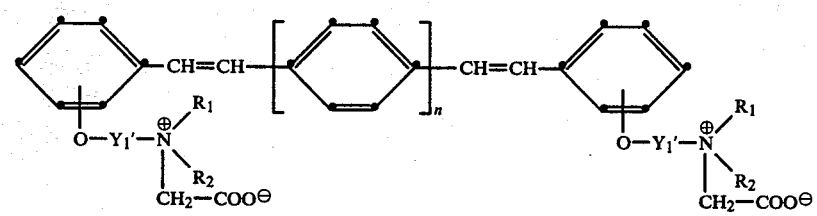

in which $Y'_1$ is $C_{1-4}$-alkylene and $R_1$, $R_2$ and n are as defined in claim 3.

5. An amphoteric styrene derivative according to claim 4, of the formula

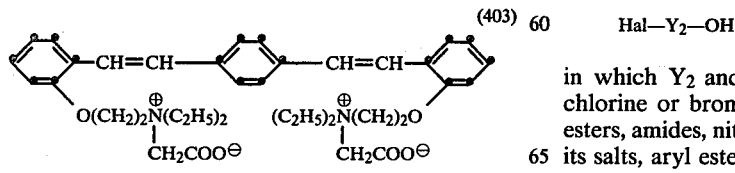

6. A process for the preparation of an amphoteric styrene derivative of the formula in which X is oxygen, sulfur, a direct bond, —SO$_2$N(-R$_5$)—, —CON(R$_5$)— or —COO—, $Y_1$ and $Y_2$ independently of one another are $C_1$-$C_4$-alkylene or hydroxypropylene, $R_1$ and $R_2$ independently of one another are $C_1$-$C_4$-alkyl or, together with the N atom, are a pyrrolidine, piperidine, hexamethyleneimine or morpholine ring, and $R_1$, together with $R_5$, is also a piperazine ring, $R_3$ and $R_4$ are hydrogen, $C_{1-4}$-alkyl, chlorine, $C_{1-4}$-alkoxy or $C_{3-4}$-alkenyl or together, in the o-position relative to one another, are a trimethylene or tetramethylene group, $R_5$ is hydrogen, $C_{1-4}$-alkyl or cyanoethyl or, together with $R_1$, is a piperazine ring, Q is —COO or —SO$_3$ and n is the number 1 or 2, which comprises reacting a styrene derivative of the formula

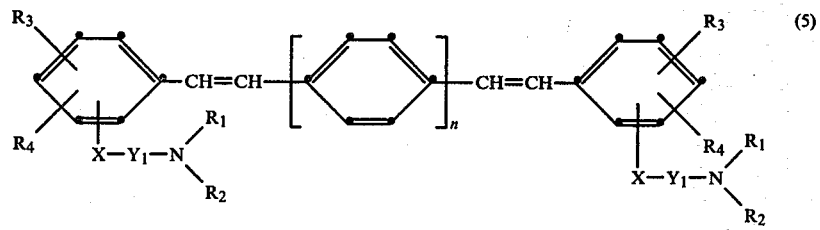

in which $R_1$, $R_2$, $R_3$, $R_4$, X, $Y_1$ and n are as defined above, with a halide of the formula Hal—Y$_2$—OH in which $Y_2$ and Q are as defined above and Hal is chlorine or bromine, or, if Q=—COO, with its salts, esters, amides, nitriles or lactones, or, if Q=—SO$_3$, with its salts, aryl esters or sultones, or, if $Y_2$=hydroxypropylene, also with the corresponding epoxides, and saponifying the quaternary ammonium halides eventually formed.

7. A process for the fluorescent brightening of organic materials, which comprises incorporating a fluorescent-brightening amount of an amphoteric styrene derivative of the formula (1) defined in claim 1, into these materials, or applying it to the surface thereof.

8. A process according to claim 7, for the fluorescent brightening of cellulose or polyacrylonitrile as organic material.

9. A detergent containing a fluorescent-brightening amount of one or more amphoteric styrene derivatives of the formula (1) defined in claim 1.

10. A detergent according to claim 9, which contains 10 to 70% by weight of a non-ionic surfactant and 1 to 30% of a cationic textile softener.

11. A detergent according to claim 10, which contains 10 to 70% by weight of a non-ionic surfactant and 1 to 30% by weight of a quaternary derivative of ammonia and/or of imidazoline, having in each case 2 long-chain aliphatic radicals, as the cationic textile softener, and a solvent to bring the detergent into the liquid form.

12. A textile treatment agent containing a fluorescent-brightening amount of one or more amphoteric styrene derivatives of the formula (1) defined in claim 1.

13. A laundry after-treatment agent containing a fluorescent-brightening amount of one or more amphoteric styrene derivatives of the formula (1) defined in claim 1, and a cationic textile softener.

14. A concentrated aqueous solution, which is stable on storage, of an amphoteric styrene derivative, which contains (a) 0.1 to 50 percent by weight of an amphoteric styrene derivative of the formula

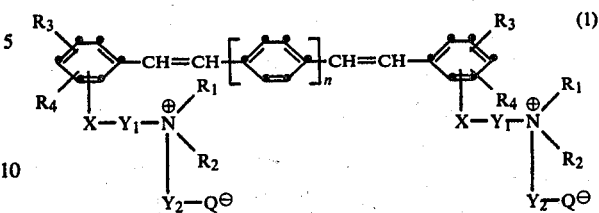

in which X is oxygen, sulfur, a direct bond, $-SO_2N(R_5-)$, $-CON(R_5-$ or $-COO-$, $Y_1$ and $Y_2$ independently of one another are $C_1-C_4$-alkylene or hydroxypropylene, $R_1$ and $R_2$ independently of one another are $C_1-C_4$-alkyl or, together with the N atom, are a pyrrolidine, piperidine, hexamethyleneimine or morpholine ring, and $R_1$, together with $R_5$, is also a piperazine ring, $R_3$ and $R_4$ are hydrogen, $C_{1-4}$-alkyl, chlorine, $C_{1-4}$-alkoxy or $C_{3-4}$-alkenyl or together, in the o-position relative to one another, are a trimethylene or tetramethylene group, $R_5$ is hydrogen, $C_{1-4}$-alkyl or cyanoethyl or, together with $R_1$, is a piperazine ring, Q is $-COO$ or $-SO_3$ and n is the number 1 or 2, (b) 0 to 20 percent by weight of the alkali metal halide formed from the quaternising agent and saponifying agent used, and (c) water.

* * * * *